United States Patent [19]
McGhee et al.

[11] Patent Number: 5,298,651
[45] Date of Patent: Mar. 29, 1994

[54] PROCESS FOR PREPARING ISOCYANATES USING PHOSPHAZINE CATALYSTS

[75] Inventors: William D. McGhee, St. Louis; Thomas E. Waldman, Chesterfield, both of Mo.

[73] Assignee: Monsanto Company, St. Louis, Mo.

[21] Appl. No.: 961,238

[22] Filed: Oct. 15, 1992

[51] Int. Cl.$^5$ .......................................... C07C 263/04
[52] U.S. Cl. ...................................... 560/345; 560/24; 560/115; 560/157; 560/336; 564/12; 564/13
[58] Field of Search ............... 560/336, 345, 24, 157, 560/115; 564/12, 13

[56] References Cited

U.S. PATENT DOCUMENTS

| | | | |
|---|---|---|---|
| 3,481,967 | 12/1969 | Ottmann et al. | 560/342 |
| 4,083,875 | 4/1978 | Schmidbaur et al. | 564/12 |
| 4,130,576 | 12/1978 | Hedaya et al. | 560/345 |
| 4,178,309 | 12/1979 | Luetzow et al. | 560/32 |
| 4,192,815 | 3/1980 | Sheludyakov et al. | 560/345 |
| 4,297,501 | 10/1981 | Becker et al. | 560/24 |
| 4,341,898 | 7/1982 | Milligan et al. | 560/24 |
| 4,388,238 | 6/1983 | Heitkämper et al. | 560/24 X |
| 4,567,294 | 1/1986 | Dressel et al. | 562/555 |
| 4,582,923 | 4/1986 | Stammann et al. | 560/24 |
| 5,063,252 | 11/1991 | Ruckes et al. | 564/13 X |
| 5,105,001 | 4/1992 | Goins et al. | 564/13 X |
| 5,189,205 | 2/1993 | McGhee et al. | 560/345 |

OTHER PUBLICATIONS

Belforte et al., *Chem. Ber.*, 121, 1891–97, (1988).

Hori et al., *Chemistry Express*, vol. 1, No. 4, pp. 224–227, (1986).

Schwesinger et al, *Agew. Chem. Int. Ed. Engl.*, 26, #1, (1987), pp. 1167–1169.

*Primary Examiner*—José G. Dees
*Assistant Examiner*—Vera C. Clarke
*Attorney, Agent, or Firm*—Kenneth D. Goetz; Paul L. Passley; James C. Bolding

[57] ABSTRACT

A process for preparing isocyanates comprising (a) contacting carbon dioxide and a primary amine in the presence of an aprotic organic solvent and a phosphazene compound or a mixture of a phosphazene compound and an organic, nitrogenous base selected from the group consisting of guanidine compounds, amidine compounds, tertiary amines, pyridine and mixtures thereof to produce the corresponding ammonium carbamate salt, and (b) reacting the ammonium carbamate salt with an electrophilic or oxophilic dehydrating agent to produce the corresponding isocyanate. A second embodiment comprises recovering the ammonium carbamate salt of step (a) prior to reacting the ammonium carbamate salt with an electrophilic or oxophilic dehydrating agent in the presence of an aprotic organic solvent and a phosphazene compound or a mixture of a phosphazene compound and an organic, nitrogenous base selected from the group consisting of guanidine compounds, amidine compounds, tertiary amines, pyridine and mixtures thereof.

24 Claims, No Drawings

PROCESS FOR PREPARING ISOCYANATES USING PHOSPHAZINE CATALYSTS

BACKGROUND OF THE INVENTION

The invention relates to a process for preparing isocyanates. In one aspect, the invention relates to a new and useful process for preparing isocyanates from primary amines, carbon dioxide and an electrophilic or oxophilic dehydrating agent.

Isocyanates, especially diisocyanates, are important commodity chemicals for use in applications such as preparation of urethane foam, urethane elastomers, coatings, insecticides, herbicides, and the like.

Commercially, the phosgenation of primary amines is by far the most widely used method for producing isocyanates. The use of phosgene, however, has several disadvantages. The phosgenation route is long, energy intensive and requires handling highly corrosive materials, e.g. hydrogen chloride, chlorine, sulfuric acid and nitric acid, and highly toxic reagents and intermediates, e.g. phosgene and chlorine. Furthermore, the phosgenation route requires use of process equipment which can withstand high temperatures and highly corrosive conditions resulting in increased capital costs.

One non-phosgene method for the preparation of isocyanates involves reaction of primary amines and $CO_2$ with a cobalt or manganese compound to produce metal carbamate complexes followed by reaction with an acyl halide in the presence of a solvent as is disclosed by A. Belforte et al., "Incorporation and Deoxygenation of Carbon Dioxide: A Metal-assisted Facile Conversion of Carbon Dioxide and Primary Amines To Isocyanates", Chem. Ber., 121, 1891–1897 (1988). However, the process described therein requires long reaction times and gives unsatisfactory yield of isocyanate for a commercially viable process.

Another non-phosgene route to isocyanates is found in U.S. Pat. No. 4,192,815 (Sheludyakov et al.) which discloses preparation of isocyanates by reacting a primary amine with $CO_2$ and hexamethyldisilazane in the presence of an acidic catalyst, e.g. $H_2SO_4$, followed by decomposition of the resulting silyl esters of carbamic acid in the presence of a dehydration agent. However, the process described therein requires long reaction times and is not commercially practicable.

A non-phosgene process for preparing isocyanates which is economical, commercially viable, and can produce isocyanates with high yield under mild reaction conditions and short reaction times is highly desirable.

SUMMARY OF THE INVENTION

It is an object of the invention to provide a process for preparing isocyanates. It is a further object of the invention to provide an efficient and economic process for preparing isocyanates that is commercially viable. It is a still further object of the invention to provide a process for preparing isocyanates which are not easily synthesized via phosgene routes.

According to the invention, a process for preparing isocyanates is provided which comprises (a) contacting carbon dioxide and a primary amine in the presence of an aprotic organic solvent and a phosphazene compound or a mixture of a phosphazene compound and an organic, nitrogenous base selected from the group consisting of guanidine compounds, amidine compounds, tertiary amines, pyridine and mixtures thereof under conditions of time and temperature sufficient to produce the corresponding ammonium carbamate salt, and (b) reacting the ammonium carbamate salt with an electrophilic or oxophilic dehydrating agent under reaction conditions of time and temperature sufficient to produce the corresponding isocyanate. In one embodiment, the ammonium carbamate salt of step (a) is recovered prior to reacting the ammonium carbamate salt with an electrophilic or oxophilic dehydrating agent in the presence of an aprotic organic solvent and a phosphazene compound or a mixture of a phosphazene compound and an organic, nitrogenous base selected from the group consisting of guanidine compounds, amidine compounds, tertiary amines, pyridine and mixtures thereof.

DETAILED DESCRIPTION OF THE INVENTION

A first embodiment of the invention relates to a process for preparing isocyanates comprising (a) contacting $CO_2$ and a primary amine in the presence of an aprotic organic solvent and a phosphazene compound or a mixture of a phosphazene compound and an organic, nitrogenous base selected from the group consisting of guanidine compounds, amidine compounds, tertiary amines, pyridine and mixtures thereof under reaction conditions of time and temperature sufficient to produce the corresponding ammonium carbamate salt, and (b) reacting the ammonium carbamate salt with an electrophilic or oxophilic dehydrating agent under reaction conditions of time and temperature sufficient to produce the corresponding isocyanate.

A second embodiment of the invention relates to a process for preparing isocyanates comprising (a) contacting $CO_2$ and a primary amine in the presence of an aprotic organic solvent and a phosphazene compound or a mixture of a phosphazene compound and an organic, nitrogenous base selected from the group consisting of guanidine compounds, amidine compounds, tertiary amines, pyridine and mixtures thereof under reaction conditions of time and temperature sufficient to produce the corresponding ammonium carbamate salt, (b) recovering the ammonium carbamate salt, and (c) reacting the ammonium carbamate salt with an electrophilic or oxophilic dehydrating agent in the presence of an aprotic organic solvent and an organic, nitrogenous base under reaction conditions of time and temperature sufficient to produce the corresponding isocyanate.

The isocyanates made according to this invention are readily recoverable and well suited for use in preparation of urethane foams, elastomers and coatings, insecticides, and herbicides.

The isocyanates produced by the process of the invention can be represented by the formula:

wherein $R_2$ is selected from the group consisting of linear or branched alkyl, alkenyl, cycloalkyl, cycloalkenyl, aryl, aralkyl, aralkenyl, alkenaryl and alkaryl radicals having 1 to about 22 carbon atoms, a radical represented by the formula:

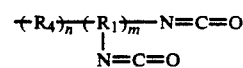

a radical represented by the formula:

a radical represented by the formula:

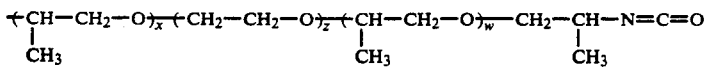

or isocyanates produced by the process of the invention can be represented by the formula:

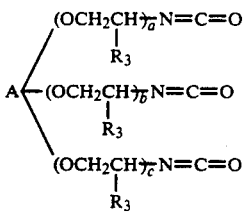

ps wherein $R_1$ and $R_4$ are independently selected from the group consisting of linear or branched alkyl, alkenyl, cycloalkyl, cycloalkenyl, aryl, aralkyl, aralkenyl, alkenaryl and alkaryl radicals having 1 to about 22 carbon atoms, m represents an integer from 0 to about 100, n represents an integer from 0 to about 8, $R_3$ is hydrogen or methyl, $x+w$ represents an integer from about 2 to about 70, z represents an integer from 0 to about 90, $x+w+z$ represents an integer from about 2 to about 100, a, b and c independently represent an integer from about 2 to about 30, and A represents a trihydric alcohol initiator such as glycerine or trimethylolpropane. In addition, $R_2$ may contain nonnucleophilic functional groups which do not react preferentially with the electrophilic or oxophilic dehydrating agent. Examples of suitable functional groups include esters, amides, urethanes, carbonates, and the like, and salts thereof.

Examples of isocyanates produced by the process of the invention include, but are not limited to, cyclohexyl isocyanate, octyl isocyanate, 4-cyclohexyl di-isocyanate, phenyl isocyanate, phenylalanine methyl ester isocyanate, glycine benzyl ester isocyanate, alanine benzyl ester isocyanate, phenylalanine ethyl ester isocyanate, leucine ethyl ester isocyanate, valine ethyl ester isocyanate, β-alanine ethyl ester isocyanate, glutamic acid diethyl ester isocyanate, hydrogenated toluene diisocyanate, hexamethylene diisocyanate, the diisocyanate of Jeffamine ® D-400, and the like, and mixtures thereof.

The ammonium salt of the carbamate anion is prepared in solution in the presence of an organic, nitrogenous base. The reaction between the primary amine and carbon dioxide to form the ammonium carbamate salt may be represented by the equation (1). The resulting ammonium carbamate salt solutions are normally homogeneous.

The result of the reaction of the ammonium carbamate salt with the electrophilic or oxophilic dehydrating agent may be represented by the equation (2).

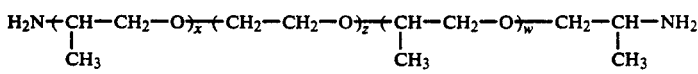

The primary amines for use in the process of the invention are selected from the group consisting of compounds represented by the formula $R-NH_2$, polyoxyalkylene diamines represented by the formula:

$$H_2N\text{-}CH\text{-}CH_2\text{-}O)_x\text{-}(CH_2\text{-}CH_2\text{-}O)_z\text{-}(CH\text{-}CH_2\text{-}O)_w\text{-}CH_2\text{-}CH\text{-}NH_2$$
with $CH_3$ groups as shown and polyoxyalkylene triamines represented by the formula:

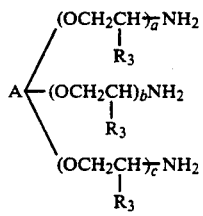

wherein R is selected from the group consisting of linear or branched alkyl, alkenyl, cycloalkyl, cycloalkenyl, aryl, aralkyl, aralkenyl, alkenaryl and alkaryl radicals having 1 to about 22 carbon atoms, a radical represented by the formula:

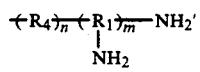

and a radical represented by the formula:

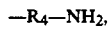

wherein $R_1$, $R_3$, $R_4$, a, b, c, m, n, w, x, z and A are as defined above. Suitable primary amines include diamines and polyamines. In addition, R may contain nonnucleophilic functional groups which do not react preferentially with the electrophilic or oxophilic dehydrating agent. Examples of suitable functional groups include esters, amides, urethanes, carbonates, and the like, and salts thereof.

Examples of primary amines which can be employed in the process of the invention include cyclohexyl amine, octyl amine, 4-diaminocyclohexane, aniline, methyl amine, ethyl amine, n-propyl amine, isopropyl amine, n-butyl amine, isobutyl amine, t-butyl amine, n-pentyl amine, isopentyl amine, n-hexyl amine, n-octyl amine, benzyl amine, phenylalanine methyl ester hydrochloride salt, glycine benzyl ester p-toluene sulphonic acid salt, alanine benzyl ester hydrochloride salt, phenyl alanine ethyl ester hydrochloride salt, leucine ethyl ester hydrochloride salt, valine ethyl ester hydrochloride salt, β-alanine ethyl ester hydrochloride salt, glutamic acid ethyl ester hydrochloride salt, 2,6-methylcyclohexyldiamine, 2,4-methylcyclohexyldiamine, n-hexyldiamine, 4,4'-methylene diphenyl amine, hexamethylene diamine, polyoxyalkylenediamines such as those available from Texaco Chemical Company under the trademark Jeffamine® including D-230 (approximate molecular weight=230), D-400 (approximate molecular weight=400), D-2000 (approximate molecular weight=2,000), D-4000 (approximate molecular weight=4,000), ED-600 (approximate molecular weight=600), ED-900 (approximate molecular weight=900), ED-2001 (approximate molecular weight=2,000), ED-4000 (approximate molecular weight=4,000) and ED-6000 (approximate molecular weight=6,000), polyoxyalkylene triamines such as those available from Texaco Chemical Company under the trademark Jeffamine® including T-403 (approximate molecular weight=440), T-3000 (approximate molecular weight=3,000) and T-5000 (approximate molecular weight=5,000), tetraethylene pentamine, diethylene triamine, triethylene tetramine, pentaethylene hexamine, and the like, and mixtures thereof.

Applicable solvents for use in the process of the invention are aprotic organic solvents. While both polar and non-polar aprotic organic solvents, as well as mixtures thereof, may be used, it is currently preferred to use non-polar aprotic organic solvents due to reduced occurrence of side reactions. As utilized herein, the phrase polar aprotic organic solvent means an aprotic organic solvent having a dielectric constant measured at 25° C. of greater than about 10 ε as reported in Reichardt, C., Solvents and solvent effects in organic chemistry, 2nd ed., VCH Verlagsgesellschaft, Weinheim, (1988), Table A-1, utilizing toluene (2.38ε) and tetrahydrofuran (7.58ε) as standards measured at 25° C. Other methods for determining dielectric constants are known and suitable polar aprotic organic solvents are those having a dielectric constant greater than that of tetrahydrofuran utilizing any of such methods.

Examples of non-polar aprotic organic solvents which can be employed in the process of the invention include dichloromethane, toluene, tetrahydrofuran, o-dichlorobenzene, triethylamine and the like, and mixtures thereof. Currently preferred non-polar aprotic organic solvents include dichloromethane and toluene.

Examples of polar aprotic organic solvents which can be employed in the process of the invention include dimethyl formamide, N-methyl-2-pyrrolidone, N,N-dimethyl acetamide, dimethyl sulfoxide, acetonitrile, sulfolane, pyridine and the like, and mixtures thereof. Currently preferred polar aprotic organic solvents include acetonitrile and N,N-dimethyl acetamide.

Although not specifically required, it is preferred to utilize the same solvent to carry out both reaction steps of the present invention in order to avoid additional process equipment for recovering additional solvents.

The amount of solvent utilized in the process of the invention is at least the amount necessary to solubilize the ammonium carbamate salt present.

To obtain high selectivities and yields for the desired isocyanates, a phosphazene compound or a mixture of a phosphazene compound and an organic, nitrogenous base is employed as the base in the process of the invention. The phrase "organic, nitrogenous base" as used herein refers to a base other than the phosphazene compound which is utilized in addition to the reactant primary amine when a mixture of a phosphazene compound and an organic, nitrogenous base is used as the base. Applicable organic, nitrogenous bases for use in the process of the invention include guanidine compounds, amidine compounds, tertiary amines, pyridine and mixtures of any two or more thereof.

The phosphazene compounds of the invention are compounds represented by the formula:

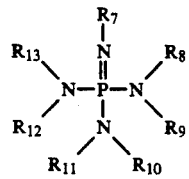

wherein $R_7$, $R_8$, $R_9$, $R_{10}$, $R_{11}$, $R_{12}$ and $R_{13}$ are independently selected from the group consisting of alkyl, aryl, alkaryl, aralkyl and cycloalkyl radicals having 1 to about 22 carbon atoms; or one of $R_8$ or $R_9$ together with one of $R_{10}$ or $R_{11}$, one of $R_{12}$ or $R_{13}$ together with one of $R_{10}$ or $R_{11}$, and $R_7$ together with one of $R_8$ or $R_9$ or one of $R_{12}$ or $R_{13}$ independently form a nitrogen-containing heterocycle; or $R_8$ together with $R_9$, $R_{10}$ together with $R_{11}$, and $R_{12}$ together with $R_{13}$ independently represent a radical represented by the formula:

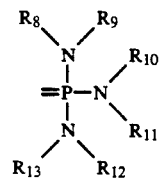

wherein $R_8$, $R_9$, $R_{10}$, $R_{11}$, $R_{12}$ and $R_{13}$ are as defined above.

Examples of phosphazene compounds which can be employed in the process of the invention include, but are not limited to, t-butyliminotris(dimethylamino)-phosphorane (P$_1$-tBu), 1-t-butyl-4,4,4-tris(dimethylamino)-2,2-bis-[tris(dimethylamino) phosphoranylideneamino]-2λ,4λ-catenadi (phosphazene)(P$_4$-tBu), 2-t-butylimino-2-diethylamino-1,3-dimethyl-perhydro-1,3,2-diazaphosphorane (BEMP), t-butyliminotris (diethylamino) phosphorane, 2-t-octylimino-2-diethylamino-1,3-dimethyl-perhydro-1,3,2-diazaphosphorane, and the like, and mixtures of any two or more thereof.

The guanidine compounds of the invention are compounds represented by the formula:

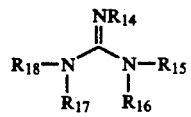

wherein $R_{14}$, $R_{15}$, $R_{16}$, $R_{17}$ and $R_{18}$ are independently selected from the group consisting of alkyl, aryl, alkaryl, aralkyl and cycloalkyl radicals having 1 to about 22 carbon atoms; or $R_{14}$ together with one of $R_{15}$, $R_{16}$, $R_{17}$ or $R_{18}$, $R_{15}$ and $R_{16}$, and $R_{17}$ and $R_{18}$ independently form a nitrogen-containing heterocycle.

The amidine compounds of the invention are compounds represented by the formula:

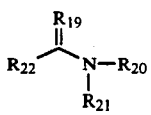

wherein $R_{19}$, $R_{20}$, $R_{21}$ $R_{22}$ are independently selected from the group consisting of alkyl, aryl, alkaryl, aralkyl and cycloalkyl radicals having 1 to about 22 carbon atoms; or $R_{19}$ together with $R_{20}$ or $R_{21}$ and $R_{22}$ together with $R_{20}$ or $R_{21}$ independently form a nitrogen-containing heterocycle.

Examples of organic, nitrogenous bases which can be employed in the process of the invention include triethylamine, diethyl isopropylamine, trimethylamine, pyridine, tetramethyl guanidine (TMG), cyclohexyl-tetramethyl guanidine (CyTMG), butyltetraethyl guanidine (n-BTEG), cyclohexyl-tetraethyl guanidine (CyTEG), tetraethyl guanidine (TEG), t-butyl-tetraethyl guanidine (t-BTEG), 7-methyl-1,5,7-triazabicyclo[4.4.0]dec-5-ene (MTBD), t-butyl-dimethyl formamidine (t-BDMF), t-butyldimethyl acetamidine (t-BDMA), 1,5-diazabicyclo[4.3.0]non-5-ene (DBN), 1,8-diazabicyclo[5.4.0]undec-7-ene (DBU) and the like, and mixtures of any two or more thereof.

The preferred organic, nitrogenous base is a guanidine compound or an amidine compound.

The amount of base, i.e., phosphazene compound or mixture of phosphazene compound and organic, nitrogenous base, utilized in the process of the invention will depend upon the particular embodiment of the process.

In the first embodiment wherein the ammonium carbamate salt is not recovered prior to reaction with the electrophilic or oxophilic dehydrating agent, the amount of base can be conveniently expressed in terms of a ratio based on the number of equivalents of amine in the primary amine charged. Broadly, the ratio of the number of moles of base to the number of equivalents of amine in the primary amine will be about 1:1 to about 20:1, preferably about 2:1 to about 10:1, and most preferably about 2:1 to about 4:1. The base can be completely charged at the beginning of the process, or a portion may be charged at the beginning of the process and the remainder charged at any time prior to the reaction of the ammonium carbamate salt with the electrophilic or oxophilic dehydrating agent.

In the second embodiment wherein the ammonium carbamate salt is recovered prior to reaction with the electrophilic or oxophilic dehydrating agent, the amount of base can be conveniently expressed in terms of a ratio based on the number of equivalents of amine in the primary amine charged for the reaction of the primary amine with carbon dioxide, and the amount of base can be conveniently expressed in terms of a ratio based on the number of equivalents of carbamate in the ammonium carbamate salt charged for the reaction of the ammonium carbamate salt with the electrophilic or oxophilic dehydrating agent. For the reaction of the primary amine with carbon dioxide, the ratio of the number of moles of base to the number of equivalents of amine in the primary amine will broadly be about 0.5:1 to about 10:1, preferably about 1:1 to about 5:1, and most preferably about 1:1 to about 2:1. For the reaction of the ammonium carbamate salt with the electrophilic or oxophilic dehydrating agent, the ratio of the number of moles of base to the number of equivalents of carbamate in the ammonium carbamate salt will broadly be about 0.5:1 to about 10:1, preferably about 1:1 to about 5:1, and most preferably about 1:1 to about 2:1.

Applicable electrophilic or oxophilic dehydrating agents for use in the process of the invention include $POX_3$, $PX_3$, $SOX_2$, $SO_2X_2$, $SO_3$, $PX_5$, $P_2O_5$, $NO_y$, $NOX$, ketene, acid anhydrides having the formula:

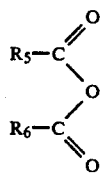

acid halides having the formula:

and halides or oxyhalides of metals selected from the group consisting of transition metals, Group III B metals, Group IV B metals, and Group V B metals, and mixtures thereof wherein $R_5$ and $R_6$ are independently selected from the group consisting of fluoroalkyl, alkyl, aryl, alkaryl and aralkyl radicals having 1 to about 22 carbon atoms, X is chlorine or bromine, halides are chlorides or bromides, and y is 1 or 2. The periodic table nomenclature used herein is that of the International Union of Pure and Applied Chemistry (IUPAC).

Examples of suitable electrophilic or oxophilic dehydrating agents include $POCl_3$, $PCl_3$, $PBr_3$, $SOCl_2$, $PCl_5$, $P_2O_5$, NO, $NO_2$, NOCl, $AlCl_3$, $VOCl_3$, $AlBr_3$, $TiBr_4$, $BBr_3$ and $TiCl_4$.

Examples of acid anhydrides which can be employed in the process of the invention include acetic anhydride, benzoic anhydride, propionoic anhydride, trifluoroacetic anhydride, and the like, and mixtures thereof. The currently preferred acid anhydride is acetic anhydride.

Examples of acid halides which can be employed in the process of the invention include acetyl chloride, acetyl bromide, benzoyl chloride, propionyl chloride, and the like, and mixtures thereof. The currently preferred acid halide is acetyl chloride.

The currently preferred electrophilic or oxophilic dehydrating agents are $POCl_3$, $PCl_3$, trifluoroacetic anhydride and $SOCl_2$ because of the extremely high yields achievable with these compounds under mild reaction conditions. However, when halide containing electrophilic or oxophilic dehydrating agents are used, halide salts are generated and must be handled as a waste byproduct. The formation of halide salt byproduct can be avoided if a non-halide containing electrophilic or oxophilic dehydrating agent, such as $P_2O_5$, acetic anhydride or $SO_3$, is used.

When phosphorus pentoxide ($P_2O_5$) is used as the electrophilic or oxophilic dehydrating agent, the $P_2O_5$ can be added to the reaction mixture as a homogeneous solution of $P_2O_5$ and a trialkylamine, e.g. triethylamine, or as a slurry in an aprotic organic solvent. Therefore, when $P_2O_5$ is charged as a homogeneous solution, the base present during the reaction of the ammonium carbamate salt with the electrophilic or oxophilic dehydrating agent will be a mixture of a phosphazene compound and a trialkylamine. When the $P_2O_5$ is charged as a homogeneous solution, the trialkylamine will be present in at least an amount sufficient to solubilize the $P_2O_5$. In addition, it has been found that the homogeneous solution can contain some water, i.e. not be substantially dry, without adversely effecting the yield of isocyanate.

In the first embodiment wherein the ammonium carbamate salt is not recovered prior to reaction with the electrophilic or oxophilic dehydrating agent, the amount of electrophilic or oxophilic dehydrating agent can be conveniently expressed in terms of a ratio based on the number of equivalents of amine in the primary amine charged. Broadly, the ratio of the number of moles of electrophilic or oxophilic dehydrating agent to the number of equivalents of amine in the primary amine will be about 0.4:1 to about 10:1, preferably about 0.9:1 to about 5:1 and most preferably about 1:1 to about 2:1.

In the second embodiment wherein the ammonium carbamate salt is recovered prior to reaction with the electrophilic or oxophilic dehydrating agent, the amount of electrophilic or oxophilic dehydrating agent can be conveniently expressed in terms of a ratio based on the number of equivalents of carbamate in the ammonium carbamate salt charged for the reaction of the ammonium carbamate salt with the electrophilic or oxophilic dehydrating agent. Broadly, the ratio of the number of moles of electrophilic or oxophilic dehydrating agent to the number of equivalents of carbamate in the ammonium carbamate salt will be about 0.4:1 to about 10:1, preferably about 0.9:1 to about 5:1, and most preferably about 1:1 to about 2:1.

The reaction between the primary amine and carbon dioxide is conducted under a $CO_2$ atmosphere. The pressure of $CO_2$ during this reaction is 0 psig (atmospheric pressure) to about 150 psig, preferably 0 psig to about 100 psig, and most preferably 0 psig to about 80 psig. It is preferred to charge the $CO_2$ to the reaction vessel containing the primary amine below the liquid level in the reaction vessel. Although not specifically required, it is preferred to conduct the reaction of ammonium carbamate salt with electrophilic or oxophilic dehydrating agent under a $CO_2$ atmosphere. However, the reaction of ammonium carbamate salt with electrophilic or oxophilic dehydrating agent can be conducted under any inert atmosphere, e.g. nitrogen, argon or air, provided the atmosphere is substantially dry. A substantially dry atmosphere is critical because water will react with the electrophilic or oxophilic dehydrating agent. The pressure during this reaction is 0 psig to about 150 psig, preferably 0 psig to about 100 psig, and most preferably 0 psig to about 80 psig.

The temperature and time used in the process of the invention will depend on the particular reaction involved. For the reaction of primary amine with $CO_2$, the temperature is about $-78°$ C. to about 100° C., preferably about 10° C. to about 40° C., and most preferably about 20° C. to about 30° C. The time will broadly be the time required to achieve complete mixing of reactants to about 4 hours, preferably about 5 minutes to about 1 hour, and most preferably about 10 minutes to about 30 minutes. For the reaction of ammonium carbamate salt with electrophilic or oxophilic dehydrating agent, the temperature is about $-78°$ C. to about 100° C., preferably about $-20°$ C. to 30° C., and most preferably about $-10°$ C. to about 10° C. The time will broadly be the time required to achieve complete mixing of the reactants to about 4 hours, preferably about 1 minute to about 30 minutes, and most preferably about 5 minutes to about 10 minutes.

For the embodiment where the ammonium carbamate salt is recovered prior to reaction with the electrophilic or oxophilic dehydrating agent, the ammonium carbamate salt can be recovered by any conventional means known in the art.

The desired isocyanates produced by the process of the invention can be recovered by any conventional means known in the art, such as that disclosed in the examples herein.

Contemplated equivalence of the general formulas set forth above for the primary amines and isocyanates are compounds otherwise corresponding thereto and having the same general properties wherein one or more of the various R groups are simple variations of the substituents as defined therein.

In addition, where a substituent is designated as, or can be, a hydrogen, the exact chemical nature of a substituent which is other than hydrogen at that position is not critical so long as it does not adversely effect the overall synthesis procedure.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable from known starting materials.

The invention will now be further disclosed in the following illustrative examples wherein parts and percentages are given on a molar basis unless otherwise specified.

EXAMPLES

All amines used in the following examples were obtained either from Aldrich Chemical Company or Kodak Chemical Company and were used as received. Acetonitrile, trifluoroacetic anhydride and triethylamine were purchased from Aldrich Chemical Company. Phosphorus oxychloride and phosphorus pentoxide was purchased from Fisher Scientific. BEMP (2-t-butylimino-2-diethylamino-1,3-dimethyl-perhydro-1,3,2-diazaphosphorane) and $P_1$-tBu (t-butyliminotris-(dimethylamino)-phosphorane) were obtained from Fluka Chemical Corp. Carbon dioxide was supplied either from Matheson (bone dry grade) or from Acetylene Gas Company (welding grade) and used without any further purification.

Gas chromatographic analysis was performed on a Varian model 3400 gas chromatograph with a model 8000 auto sampler using a 30 meter Megabore DB-1 (3 $\mu$m) J&W Scientific column.

EXAMPLE 1

This example demonstrates the production of octyl isocyanate from octyl amine using BEMP as the base and trifluoroacetic anhydride as the "dehydrating agent".

A Fischer-Porter bottle was charged with 0.65 g (5 mmol) of octyl amine, 2.74 g of BEMP (10 mmol), 25 mL of acetonitrile and 184 mg (1 mmol) of tridecane as an internal standard. The bottle was pressurized to 80 psig with carbon dioxide and the solution was stirred for 30 min. at room temperature. A second Fischer-Porter bottle was charged with 0.71 mL (5 mmol) of trifluoroacetic anhydride and 25 mL of acetonitrile then pressurized to 80 psig with $CO_2$. The two solutions were cooled to 0° C. in an ice bath for 10 minutes after which time the octyl carbamate solution was added rapidly to the trifluoroacetic anhydride solution. An aliquot was taken after five minutes and diluted with diethyl ether prior to G.C. analysis which indicated a yield of 83% octyl isocyanate. The reaction mixture was allowed to warm slowly to room temperature and aliquots were taken periodically for G.C. analysis. A maximum yield of 85% octyl isocyanate was obtained after ca. 30 minutes.

EXAMPLE 2

This example demonstrates the production of 2,4-2,6-diisocyanatomethylcyclohexane from 2,4-2,6-diaminomethylcyclohexane using BEMP as the base and trifluoroacetic anhydride as the "dehydrating agent".

A Fischer-Porter bottle was charged with 0.65 g (5 mmol) of 2,4-2,6-diaminomethylcyclohexane (80% 2,4-isomer, 20% 2,6-isomer), 5.49 g of BEMP (20 mmol), 25 mL of acetonitrile and 184 mg (1 mmol) of tridecane as an internal standard. The bottle was pressurized to 80 psig with carbon dioxide and the solution was stirred for 30 minutes at room temperature. A second Fischer-Porter bottle was charged with 1.42 mL (10 mmol) of trifluoroacetic anhydride and 25 mL of acetonitrile then pressurized to 80 psig with $CO_2$. The two solutions were cooled to 0° C. in an ice bath for 10 minutes after which time the octyl carbamate solution was added rapidly to the trifluoroacetic anhydride solution. An aliquot was taken after five minutes and diluted with diethyl ether prior to G.C. analysis which indicated a yield of 63% 2,4-2,6-diisocyanatomethylcyclohexane. Aliquots were taken for G.C. analysis over several hours and showed no change in the yield of the diisocyanate.

EXAMPLE 3

This example demonstrates the production of cyclohexyl isocyanate from cyclohexylamine using $P_1$-tBu as the base and phosphorus oxychloride as the "dehydrating agent".

A Fischer-Porter bottle was charged with 0.15 g (1.5 mmol) of cyclohexyl amine, 0.99 g of $P_1$-tBu (3 mmol), 10 mL of acetonitrile and 71 mg (0.5 mmol) of tridecane as an internal standard. The bottle was pressurized to 80 psig with carbon dioxide and the solution was stirred for 30 minutes at room temperature. A second Fischer-Porter bottle was charged with 0.14 mL (1.5 mmol) of phosphorus oxychloride and 10 mL of acetonitrile then pressurized to 80 psig with $CO_2$. The two solutions were cooled to 0° C. in an ice bath for 10 minutes after which time the cyclohexyl carbamate solution was added rapidly to the $POCl_3$ solution. An aliquot was taken after five minutes and diluted with diethyl ether prior to G.C. analysis which indicated a yield of 98% cyclohexyl isocyanate.

EXAMPLE 4

This example demonstrates the production of octyl isocyanate from octyl amine using $P_1$-tBu as the base and $P_2O_5$ as the "dehydrating agent".

A Fischer-Porter bottle was charged with 1.29 g (10 mmol) of octyl amine, 2.34 g of $P_1$-tBu (10 mmol), 10 mL of acetonitrile and 154 mg (1 mmol) of biphenyl as an internal G.C. standard. The bottle was pressurized to 20 psig with carbon dioxide and the solution was stirred for 45 minutes at room temperature. A second Fischer-Porter bottle was charged with 2 g (14 mmol) of $P_2O_5$ and 10 mL of acetonitrile followed by the addition of 2 g (20 mmol) triethylamine. The $P_2O_5$/triethylamine mixture gave a dark brown solution which was pressurized to 20 psig with carbon dioxide. The carbamate solution was added rapidly to this mixture at room temperature. An aliquot was taken after five minutes and diluted with diethyl ether prior to G.C. analysis which indicated a yield of 16% octyl isocyanate. The reaction mixture was analyzed again after 2 hours (87% isocyanate) and 16 hours (93% isocyanate).

EXAMPLE 5

This example demonstrates the production of octyl isocyanate from octyl amine using $P_1$-tBu as the base and $P_2O_5$ as the "dehydrating agent".

A Fischer-Porter bottle was charged with 0.65 g (5 mmol) of octyl amine, 1.17 g of $P_1$-tBu (5 mmol), 0.51 g of triethylamine, 25 mL of acetonitrile and 184 mg (1 mmol) of tridecane as an internal standard. The bottle was pressurized to 80 psig with carbon dioxide and the solution was stirred for 30 minutes at room temperature. A second Fischer-Porter bottle was charged with 4 g (28 mmol) of $P_2O_5$ (phosphorus pentoxide), 0.86 mL water, 4 mL of triethylamine and 25 mL of acetonitrile then pressurized to 80 psig with $CO_2$. The $P_2O_5$/water/triethylamine mixture gave a dark brown solution and the carbamate solution was added rapidly to this mixture at room temperature. An aliquot was taken after five minutes and diluted with diethyl ether prior to G.C. analysis which indicated a yield of 15% octyl isocyanate. The reaction mixture was stirred for an additional 18 hours during which time the yield of octyl isocyanate increased to 98.8% by G.C. analysis.

The results indicate that water present in the homogeneous solution of $P_2O_5$ in triethylamine does not adversely effect the yield of isocyanate.

EXAMPLE 6

This example demonstrates the production of octyl isocyanate from octyl amine using $P_1$-tBu as the base and $SO_3$-$NMe_3$ as the "dehydrating agent".

A Fischer-Porter bottle was charged with 0.55 g (4.2 mmol) of octyl amine, 0.99 g of $P_1tBu$ (3 mmol), 25 mL of acetonitrile and 130 mg (0.84 mmol) of tridecane as an internal standard. The bottle was pressurized to 80 psig with carbon dioxide and the solution was stirred for 30 min. at room temperature. A second Ficher-Porter bottle was charged with 0.65 g (4.7 mmol) of sulfur trioxide trimethylamine adduct ($SO_3$-$NMe_3$) and 20 mL of acetonitrile then pressurized to 80 psig with $CO_2$. The two solutions were cooled to 0° C. in an ice bath for 10 min after which time the octyl carbamate solution was added rapidly to the $SO_3$-$NMe_3$ suspension. An aliquot was taken after five minutes and diluted with diethyl ether prior to G.C. analysis which indicated a yield of 11% octyl isocyanate. Further monitoring of the reaction progress over 48 hrs gave a maximum yield of 27% octyl isocyanate.

EXAMPLE 7

This example demonstrates the production of octyl isocyanate from octyl amine using a mixture of $P_1$-tBu and triethylamine as the base and $P_2O_5$ as the "dehydrating agent".

A Fischer-Porter bottle was charged with 0.65 g (5 mmol) of octyl amine, 1.17 g of $P_1$-tBu (5 mmol), 1.02 g (10 mmol) of triethylamine, 25 mL of acetonitrile and 154 mg (1 mmol) of biphenyl as an internal standard. The bottle was pressurized to 80 psig with carbon dioxide and the solution was stirred for 30 min. at room temperature. A second Fischer-Porter bottle was charged with 2.82 g (20 mmol) of phosphorus pentoxide, and 25 mL of acetonitrile then pressurized to 80 psig with $CO_2$. The carbamate solution was added rapidly to the $P_2O_5$ suspension at room temperature causing the $P_2O_5$ to dissolve. An aliquot was taken after three minutes and diluted with diethyl ether prior to G.C analysis which indicated a quantitative yield of octyl isocyanate.

EXAMPLE 8

This example demonstrates the production of octyl isocyanate from octyl amine using a mixture of $P_1$-tBu and triethylamine as the base and $P_2O_5$ as the "dehydrating agent".

A Fischer-Porter bottle was charged with 0.65 g (5 mmol) of octyl amine, 1.17 g of $P_1$-tBu (5 mmol), 1 02 g (10 mmol) of triethylamine, 25 mL of acetonitrile and 154 mg (1 mmol) of biphenyl as an internal standard. The bottle was pressurized to 80 psig with carbon dioxide and the solution was stirred for 30 min. at room temperature. A second Fischer-Porter bottle was charged with 0.71 g (5 mmol) of phosphorus pentoxide, and 25 mL of acetonitrile then pressurized to 80 psig with $CO_2$. The carbamate solution was added rapidly to the $P_2O_5$ suspension at room temperature causing the $P_2O_5$ to dissolve. An aliquot taken after three minutes gave a 22% yield of octyl isocyanate by G.C. analysis. The reaction was monitored for a total of 18 hrs during which time the yield of octyl isocyanate increased to a maximum of 27% (1 hr) and then steadily decreased with formation of the symmetric urea.

EXAMPLE 9

This example demonstrates the production of octyl isocyanate from octyl amine using a mixture of $P_1$-tBu and triethylamine as the base and $P_2O_5$ as the "dehydrating agent".

A Fischer-Porter bottle was charged with 0.65 g (5 mmol) of octyl amine, 1.17 g of $P_1$-tBu (5 mmol), 1.02 g (10 mmol) of triethylamine, 25 mL of dichloromethane and 154 mg (1 mmol) of biphenyl as an internal standard. The bottle was pressurized to 80 psig with carbon dioxide and the solution was stirred for 30 min. at room temperature. A second Fischer-Porter bottle was charged with 1.41 g (10 mmol) of phosphorus pentoxide, and 25 mL of dichloromethane then pressurized to 80 psig with $CO_2$. The carbamate solution was added rapidly to the $P_2O_5$ suspension at room temperature causing the $P_2O_5$ to dissolve. An aliquot was taken after five minutes and diluted with diethyl ether prior to G.C. analysis which indicated 82% yield of octyl isocyanate. A maximum yield of 94% octyl isocyanate was achieved after ca. 1 hr at room temperature.

EXAMPLE 10

This example demonstrates the production of octyl isocyanate from octyl amine using a mixture of $P_1$-tBu and triethylamine as base and $P_2O_5$ as the "dehydrating agent".

A Fischer-Porter bottle was charged with 0.65 g (5 mmol) of octyl amine, 1.17 g of $P_1$-tBu (5 mmol), 1.02 g (10 mmol) of triethylamine, 25 mL of acetonitrile and 154 mg (1 mmol) of biphenyl as an internal standard. The bottle was pressurized to 80 psig with carbon dioxide and the solution was stirred for 30 min. at room temperature. A second Fischer-Porter bottle was charged with 14.1 g (50 mmol) of phosphorus pentoxide, and 25 mL of acetonitrile then pressurized to 80 psig with $CO_2$. The carbamate solution was added rapidly to the $P_2O_5$ suspension at room temperature causing some of the $P_2O_5$ to dissolve. An aliquot taken after three minutes gave a 89% yield of octyl isocyanate by G.C. analysis. The reaction was monitored for a total of 18 hrs during which time the yield of octyl isocyanate increased to a maximum of 97% (2.5 hr).

That which is claimed is:

1. A process for preparing an isocyanate comprising:
   (a) contacting $CO_2$ and a primary amine in the presence of an aprotic organic solvent and a base selected from the group consisting of a phosphazene compound and a mixture of a phosphazene compound and an organic, nitrogenous base wherein said organic, nitrogenous base is selected from the group consisting of guanidine compounds, amidine compounds, tertiary amines, pyridine and mixtures thereof, under reaction conditions of time and temperature sufficient to produce the corresponding ammonium carbamate salt, and
   (b) reacting said ammonium carbamate salt with an electrophilic or oxophilic dehydrating agent selected from the group consisting of $POX_3$, $PX_3$, $SOX_2$, $SO_2X_2$, $PX_5$, $P_2O_5$, $NO_y$, $NOX$, ketene, acid anhydrides having the formula:

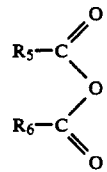

acid halides having the formula:

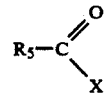

and halides or oxyhalides of metals selected from the group consisting of transition metals, Group III B metals, Group IV B metals, and Group V B metals, wherein $R_5$ and $R_6$ are independently selected from the group consisting of alkyl, fluoroalkyl, aryl, alkaryl and aralkyl radicals having 1 to about 22 carbon atoms, X is chlorine or bromine, halides are chlorides or bromides, and y is 1 or 2 under reaction conditions of time and temperature sufficient to produce the corresponding isocyanate wherein said phosphazene compound is represented by the formula:

compounds represented by the formula R—NH$_2$, polyoxyalkylene diamines represented by the formula:

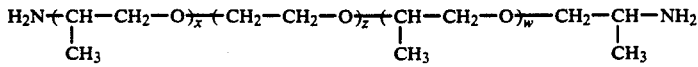

and polyoxyalkylene triamines represented by the formula:

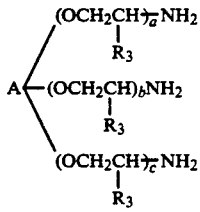

wherein R is selected from the group consisting of alkyl, alkenyl, cycloalkyl, cycloalkenyl, aryl, aralkyl, aralkenyl, alkenaryl and alkaryl radicals having 1 to about 22 carbon atoms, a radical represented by the formula:

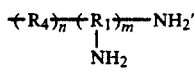

and a radical represented by the formula —R$_4$—NH$_2$, or R as defined above containing nonnucleophilic functional groups; wherein R$_1$ and R$_4$ are independently selected from the group consisting of alkyl, alkenyl, cycloalkyl, cycloalkenyl, aryl, aralkyl, aralkenyl, alkenaryl and alkaryl radicals having 1 to about 22 carbon atoms, m represents an integer from 0 to about 100, n represents integer from 0 to about 8, R$_3$ is hydrogen or methyl, x+w represents an integer from about 2 to about 70, z represents an integer from 0 to about 90, x+w+z represents an integer from about 2 to about 100, a, b and c independently represent an integer from about 2 to about 30, and A represents a trihydric alcohol initiator.

10. The process according to claim 8 wherein said nonnucleophilic functional groups are selected from the group consisting of esters, amides, urethanes, carbonates and salts thereof.

11. A process according to claim 1 wherein said isocyanate is represented by the formula:

R$_2$—N=C=O wherein R$_2$ is selected from the group consisting of alkyl, alkenyl, cycloalkyl, cycloalkenyl, aryl, aralkyl, aralkenyl, alkenaryl and alkaryl radicals having 1 to about 22 carbon atoms, a radical represented by the formula:

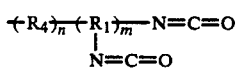

a radical represented by the formula:

—R$_4$—N=C=O, a radical represented by the formula:

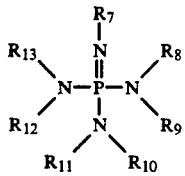

wherein R$_7$, R$_8$, R$_9$, R$_{10}$, R$_{11}$, R$_{12}$ and R$_{13}$ are independently selected from the group consisting of alkyl, aryl, alkaryl, aralkyl and cycloalkyl radicals having 1 to about 22 carbon atoms; or one of R$_8$ or R$_9$ together with one of R$_{10}$ or R$_{11}$, one of R$_{12}$ or R$_{13}$ together with one of R$_{10}$ or R$_{11}$, and R$_7$ together with one of R$_8$ or R$_9$ or one of R$_{12}$ or R$_{13}$ independently form a nitrogen-containing heterocycle; or R$_8$ together with R$_9$, R$_{10}$ together with R$_{11}$, and R$_{12}$ together with R$_{14}$ independently represent a radical represented by the formula:

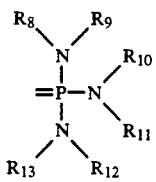

2. The process according to claim 1 wherein said aprotic organic solvent is selected from the group consisting of dichloromethane, tetrahydrofuran, acetonitrile, o-dichlorobenzene, toluene, N,N-dimethylacetamide and pyridine.

3. The process according to claim 2 wherein said aprotic organic solvent is present in at least an amount sufficient to solubilize said ammonium carbamate salt.

4. The process according to claim 1 wherein said electrophilic or oxophilic dehydrating agent is selected from the group consisting of POCl$_3$, SOCl$_2$, P$_2$O$_5$, SO$_2$Cl$_2$, acetic anhydride, acetyl chloride, SO$_3$, PCl$_3$, trifluoroacetic anhydride, TiBr$_4$, AlCl$_3$, VOCl$_3$ and BBr$_3$.

5. The process according to claim 1 wherein said base is t-butyliminotris (dimethylamino)phosphorane or 2-t-butylimino-2-diethylamino-1,3-dimethyl-perhydro-1,3,2-diazaphosphorane.

6. The process according to claim 1 wherein the ratio of the number of moles of said base to the number of equivalents of amine in said primary amine starting material is 1:1 to about 20:1.

7. The process according to claim 6 wherein the ratio of the number of moles of said base to the number of equivalents of amine in said primary amine starting material is about 2:1 to about 10:1.

8. The process according to claim 6 wherein the ratio of the number of moles of said electrophilic or oxophilic dehydrating agent to the number of equivalents of amine in said primary amine starting material is about 0.4:1 to about 10:1.

9. The process according to claim 1 wherein said primary amine is selected from the group consisting of

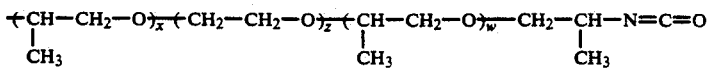

or $R_2$ as defined above containing nonnucleophilic functional groups; or said isocyanate is represented by the formula:

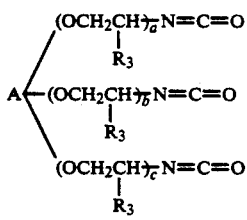

wherein $R_1$ and $R_4$ are independently selected from the group consisting of alkyl, alkenyl, cycloalkyl cycloalkenyl, aryl, aralkyl, aralkenyl, alkenaryl and alkaryl radicals having 1 to about 22 carbon atoms, m represents an integer from 0 to about 100, n represents an integer from 0 to about 8, $R_3$ is hydrogen or methyl, $x+w$ represents an integer from about 2 to about 10, z represents an integer from 0 to about 90, $x+w+z$ represents an integer from about 2 to about 100, a, b and c independently represent an integer from about 2 to about 30, and A represents a trihydric alcohol initiator.

12. The process according to claim 10 wherein said nonnucleophilic functional groups are selected from the group consisting of esters, amides, urethanes, carbonates and salts thereof.

13. A process for preparing an isocyanate comprising:
(a) contacting $CO_2$ and a primary amine in the presence of an aprotic organic solvent and a base selected from the group consisting of a phosphazene compound and a mixture of a phosphazene compound and an organic, nitrogenous base wherein said organic, nitrogenous base is selected from the group consisting of guanidine compounds, amidine compounds, tertiary amines, pyridine and mixtures thereof, under reaction conditions of time and temperature sufficient to produce the corresponding ammonium carbamate salt,
(b) recovering said ammonium carbamate salt, and
(c) reacting said ammonium carbamate salt with an electrophilic or oxophilic dehydrating agent selected from the group consisting of $POX_3$, $PX_3$, $SOX_2$, $SO_2X_2$, $PX_5$, $P_2O_5$, $NO_y$, NOX, ketene, acid anhydrides having the formula:

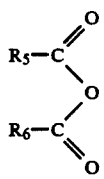

acid halides having the formula:

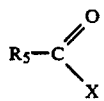

and halides or oxyhalides of metals selected from the group consisting of transition metals, Group III B metals, Group IV B metals, and Groups V B metals, wherein $R_5$ and $R_6$ are independently selected from the group consisting of alkyl, fluoroalkyl, aryl, alkaryl and aralkyl radicals having 1 to about 22 carbon atoms, X is chlorine or bromine, halides are chlorides or bromides, and y is 1 or 2 in the presence of an aprotic organic solvent and a base selected from the group consisting of a phosphazene compound and a mixture of a phosphazene compound and an organic, nitrogenous base wherein said organic, nitrogenous base is selected from the group consisting of guanidine compounds, amidine compounds, tertiary amines, pyridine and mixtures thereof, under reaction conditions of time and temperature sufficient to produce the corresponding isocyanate wherein said phosphazene compound is represented by the formula:

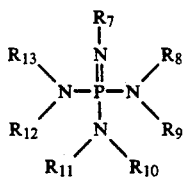

wherein $R_7$, $R_8$, $R_9$, $R_{10}$, $R_{11}$, $R_{12}$ and $R_{13}$ are independently selected from the group consisting of alkyl, aryl, alkaryl, aralkyl and cycloalkyl radicals having 1 to about 22 carbon atoms; or one of $R_8$ or $R_9$ together with one of $R_{10}$ or $R_{11}$, one of $R_{12}$ or $R_{13}$ together with one of $R_{10}$ or $R_{11}$, and $R_7$ together with one of $R_8$ or $R_9$ or one of $R_{12}$ or $R_{13}$ independently form a nitrogen-containing heterocycle; or $R_8$ together with $R_9$, $R_{10}$ together with $R_{11}$, and $R_{12}$ together with $R_{13}$ independently represent a radical represented by the formula:

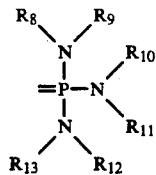

wherein $R_8$, $R_9$, $R_{10}$, $R_{11}$, $R_{12}$ and $R_{13}$ are as defined above.

14. The process according to claim 13 wherein said aprotic organic solvent is selected from the group consisting of dichloromethane, tetrahydrofuran, acetonitrile, o-dichlorobenzene, toluene, N,N-dimethylacetamide and pyridine.

15. The process according to claim 14 wherein said aprotic organic solvent is present in at least an amount sufficient to solubilize said ammonium carbamate salt.

16. The process according to claim 13 wherein said electrophilic or oxophilic dehydrating agent is selected from the group consisting of $POCl_3$, $SOCl_2$, $P_2O_5$, $SO_2Cl_2$, acetic anhydride, acetyl chloride, $SO_3$, $PCl_3$, trifluoroacetic anhydride, $TiBr_4$, $AlCl_3$, $VOCl_3$ and $BBr_3$.

17. The process according to claim 13 wherein said base is t-butyliminotris (dimethylamino)-phosphorane or 2-t-butylimino-2-diethylamino-1,3-dimethyl-perhydro-1,3,2-diazaphosphorane.

18. The process according to claim 12 wherein the ratio of the number of moles of said base to the number of equivalents of amine in said primary amine starting material in step (a) is 0.5:1 to about 10:1, and the ratio of the number of moles of said base to the number of equivalents of carbamate in said ammonium carbamate salt starting material in step (c) is 0.5:1 to about 10:1.

19. The process according to claim 18 wherein the ratio of the number of moles of said base to the number of equivalents of amine in said primary amine starting material in step (a) is 1:1 to about 5:1, and the ratio of the number of moles of said base to the number of equivalents of carbamate in said ammonium carbamate salt starting material in step (c) is 1:1 to about 5:1.

20. The process according to claim 18 wherein the ratio of the number of moles of said electrophilic or oxophilic dehydrating agent to the number of equivalents of carbamate in said ammonium carbamate salt starting material in step (c) is about 0.4:1 to about 10:1.

21. The process according to claim 13 wherein said primary amine is selected from the group consisting of compounds represented by the formula R—NH$_2$, polyoxyalkylene diamines represented by the formula:

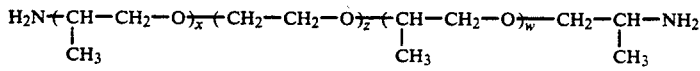

and polyoxyalkylene triamines represented by the formula:

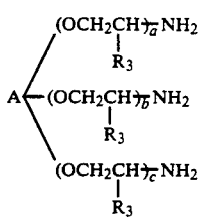

wherein R is selected from the group consisting of alkyl, alkenyl, cycloalkyl, cycloalkenyl, aryl, aralkyl, aralkenyl, alkenaryl and alkaryl radials having 1 to about 22 carbon atoms, a radial represented by the formula:

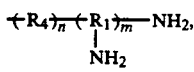

a radical represented by the formula —R$_4$—NH$_2$, or R as defined above containing nonnucleophilic functional groups;
wherein R$_1$ and R$_4$ are independently selected from the group consisting of alkyl, alkenyl, cycloalkyl, cycloalkenyl, aryl, aralkyl, aralkenyl, alkenaryl and alkaryl radicals having 1 to about 22 carbon atoms, m represents an integer from 0 to about 100, n represents an integer from 0 to about 8, R$_3$ is hydrogen or methyl, x+w represents an integer from about 2 to about 70, z represents an integer from 0 to about 90, x+w+z represents an integer from about 2 to about 100, a, b and c independently represent an integer from about 2 to about 30, and A represents a trihydric alcohol initiator.

22. The process according to claim 21 wherein said nonnucleophilic functional groups are selected from the group consisting of esters, amides, urethanes, carbonates and salts thereof.

23. A process according to claim 13 wherein said isocyanate is represented by the formula:

$$R_2-N=C=O$$

wherein R$_2$ is selected from the group consisting of alkyl, alkenyl, cycloalkyl, cycloalkenyl, aryl, aralkyl, aralkenyl, alkenaryl and alkaryl radicals having 1 to about 22 carbon atoms, a radical represented by the formula:

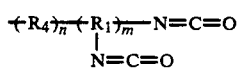

a radical represented by the formula:

$$-R_4-N=C=O,$$

a radical represented by the formula:

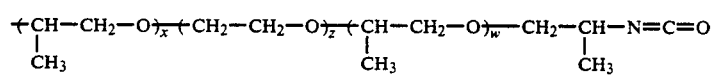

or R$_2$ as defined above containing nonnucleophilic functional groups; or said isocyanate is represented by the formula:

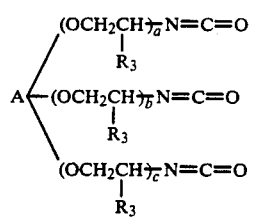

wherein R$_1$ and R$_4$ are independently selected from the group consisting of alkyl, alkenyl, cycloalkyl, cycloalkenyl, aryl, aralkyl, aralkenyl, alkenaryl and alkaryl radicals having 1 to about 22 carbon atoms, m represents an integer from 0 to about 100, n represents an integer from 0 to about 8, R$_3$ is hydrogen or methyl, x+w represents an integer from about 2 to about 70, z represents an integer from 0 to about 90, x+w+z represents an integer from about 2 to about 100, a, b and c independently represent an integer from about 2 to about 30, and A represents a trihydric alcohol initiator.

24. The process according to claim 23 wherein said nonnucleophilic functional groups are selected from the group consisting of esters, amides, urethanes, carbonates and salts thereof.

* * * * *

UNITED STATES PATENT AND TRADEMARK OFFICE
CERTIFICATE OF CORRECTION

PATENT NO. : 5,298,651

DATED : March 29, 1994

INVENTOR(S) : William D. McGhee and Thomas E. Waldman

It is certified that error appears in the above-identified patent and that said Letters Patent is hereby corrected as shown below:

On the title page, item [54]:
In the title delete "Phosphazine Catalysts" and insert therefor --- Phosphazene Bases ---.

Signed and Sealed this

Thirtieth Day of August, 1994

Attest:

BRUCE LEHMAN

Attesting Officer

Commissioner of Patents and Trademarks